(12) United States Patent
Grimm

(10) Patent No.: US 6,855,120 B2
(45) Date of Patent: Feb. 15, 2005

(54) APHERESIS SYSTEM WITH ANTICOAGULANT FLOW CONTROL

(75) Inventor: Daniel J. Grimm, McHenry, IL (US)

(73) Assignee: Baxter International Inc., Deerfield, IL (US)

(*) Notice: Subject to any disclaimer, the term of this patent is extended or adjusted under 35 U.S.C. 154(b) by 163 days.

(21) Appl. No.: 10/372,882

(22) Filed: Feb. 24, 2003

(65) Prior Publication Data

US 2003/0175150 A1 Sep. 18, 2003

Related U.S. Application Data

(63) Continuation of application No. 09/042,260, filed on Mar. 13, 1998, now Pat. No. 6,565,806.

(51) Int. Cl.⁷ .......................... A61M 37/00; A61M 1/14
(52) U.S. Cl. .................... 604/6.07; 604/6.01; 604/6.16; 422/44
(58) Field of Search .................... 604/4.01, 5.01, 604/6.01–6.04, 6.07, 6.1, 6.11, 6.16, 19, 30, 31, 65, 264, 523, 537, 80, 83; 422/44; 210/645–646, 781–782; 435/35

(56) References Cited

U.S. PATENT DOCUMENTS

| | | | |
|---|---|---|---|
| 4,469,483 A | 9/1984 | Becker et al. | |
| 4,526,515 A | 7/1985 | DeVries | |
| 4,547,186 A | 10/1985 | Bartlett | |
| 4,551,131 A | 11/1985 | Miles et al. | |
| 5,015,226 A | 5/1991 | Polaschegg | |
| 5,378,227 A | 1/1995 | O'Riordan et al. | |
| 5,817,042 A | 10/1998 | Langley et al. | |
| 6,033,561 A | 3/2000 | Schoendorfer | |

OTHER PUBLICATIONS

Baxter Healthcare Corp., Fenwal Division, "Product Update," Closed system apheresis kit does double duty, 2 pages.

Baxter Healthcare Corp., Fenwal Division, "Product Update," Closed system single access apheresis kit, 2 pages.

Baxter Healthcare Corp., Fenwal Division, "Product Update," Dual needle return line adds value to apheresis kit, 2 pages.

Declaration of Daniel J. Grimm, 3 pages.

*Primary Examiner*—Patricia Bianco
(74) *Attorney, Agent, or Firm*—Bradford R. L. Price; Gary W. McFarron

(57) ABSTRACT

An apheresis system is disclosed which may include a separation chamber; a suspension flow path which communicates at one end with the separation chamber and includes a connector at the other end for connecting to a source of cellular suspension; an anticoagulant flow path which communicates at one end with the suspension flow path and includes a connector at the other end for connecting to an anticoagulant source; and a return flow path which communicates at one end with the separation chamber and communicates at the other end with a connector for connection directly to the suspension source or to the suspension flow path for returning one or more suspension components to the source. The anticoagulant flow path includes a flow restriction, such as an internal flow restriction, which limits the free flow of anticoagulants into the suspension flow path while preferably not completely stopping the flow of anticoagulant. The restriction may take various forms, but the preferred construction comprises a tubing segment of reduced inside diameter, providing resistance to the free flow of anticoagulant in the event of operator error or mechanical failure.

11 Claims, 2 Drawing Sheets

APHERESIS SYSTEM WITH ANTICOAGULANT FLOW CONTROL

This is a continuation of patent application Ser. No. 09/042,260, filed Mar. 13, 1998 now U.S. Pat. No. 6,565,806.

The present invention generally relates to apheresis systems for separating one or more components from a cellular suspension such as blood. More specifically, the present invention relates to an improved apheresis system that limits the free flow of anticoagulant in the event of improper assembly or mechanical failure of the apheresis system.

The separation of blood into one or more component parts, such as platelets, red cells or plasma, has been well known for many years. Within the past twenty years, automated apheresis systems, which automatically process the blood of a donor or patient, separate out the desired blood component and return the remainder to the donor/patient, have become commonplace in developed countries.

Typically such automated apheresis systems employ a fluid circuit assembly, for example, a pre-assembled disposable plastic tubing and container set, which is mounted on a reusable hardware device. The reusable hardware device includes pumps, monitors, drive systems and the like for carrying out, in combination with the disposable fluid circuit assembly or system, a blood apheresis procedure.

There are several different automated apheresis systems commercially available. Baxter Healthcare Corporation, a pioneer in the field of automated blood apheresis, manufactures and sells the CS-3000 and Amicus centrifugal apheresis systems and the "Autopheresis C," which is a non-centrifugal system, based on a different principle of blood separation. The Baxter CS-3000, Amicus and Autopheresis C apheresis systems are described, for example, in U.S. Pat. Nos. 4,526,515; 5,427,509; and 5,194,145, respectively, which are incorporated by reference. Centrifugal apheresis systems are also available from Cobe Laboratories Inc., which markets the Spectra apheresis system, and Haemonetics Corporation.

One of the characteristics of human blood is that it begins to clot immediately upon leaving the human vascular system. Accordingly, in automated apheresis systems, anticoagulant is used to prevent the donor/patient's blood from clotting as it is processed through the fluid circuit of the apheresis system. One of the most common anticoagulants is ACD, (anticoagulant citrate dextrose), which is commercially available in various formulations. In automated apheresis systems, ACD is typically metered into the whole blood immediately after the blood is withdrawn from the donor/patient.

The amount of anticoagulant and the rate at which it is added to the donor/patient's blood represents a balance of competing considerations. On the one hand, it is desirable to add sufficient anticoagulant so that the blood and blood components do not clot or clump as they are processed through the fluid circuit of the apheresis system. On the other hand, the flow rate of anticoagulant can not be too great or it will cause adverse reaction in the donor/patient.

A portion of the anticoagulant that is mixed with the whole blood is also returned to the donor/patient together with the blood components being returned. Specifically, the anticoagulant that is not removed with the blood components being collected is returned to the donor/patient with the remaining blood components. Although ACD anticoagulant is metabolized by the human body, if anticoagulant is returned to the donor/patient too fast it can, in fact, cause adverse reactions. Depending on the amount rate of anticoagulant returned, these reactions can range from mild physical symptoms, such as tingling of the lips or extremities, to potential actual harm to the donor/patient.

Accordingly, automated apheresis systems typically use pumps to control and meter the flow of anticoagulant added to the whole blood. The pumps used are commonly peristaltic pumps. Peristaltic pumps use a series of spaced apart rollers that progressively pinch or squeeze the tubing to force fluid flow therethrough. When the tubing is properly installed in cooperation with the pump, peristaltic pumps tend to be very reliable and relatively accurate. Moreover, in the event of system shutdown or the like, at least one roller occludes the tubing to prevent undesired flow past the pump.

Although the manufacturers of automated apheresis systems have taken a variety of precautions by way of safety sensors and detectors to safeguard the donor/patient from operator inadvertence or error, continued diligence in identifying potential failure modes of apheresis systems has identified one scenario in which operator inattention or misassembly may result in larger than desired anticoagulant flow rates into the whole blood withdrawn from the donor/patient, with the potential result that more anticoagulant is returned to the donor/patient than is desirable.

More particularly, this scenario may occur if operator inattention or misassembly results in improper or incomplete installation of the anticoagulant tubing with the anticoagulant pump. In the typical apheresis system, the anticoagulant or ACD container is hung from a rack located over the apheresis device and above the donor/patient. This creates a liquid head of anticoagulant which, if not properly controlled by a pump, may cause an unrestricted or free flow of anticoagulant into the whole blood being withdrawn from the donor or patient. In other words, if the anticoagulant pump tubing segment is not properly engaged with the rollers of the pump, an open flow path may result, allowing an uncontrolled and free flow of excessive amounts of anticoagulant into the whole blood flow path. The result is an excess of anticoagulant being returned to the donor/patient, causing possible adverse reactions.

SUMMARY OF THE INVENTION

The present invention is directed to an apheresis system which, in the event of incomplete or improper installation of the anticoagulant tubing, whether by operator or mechanical failure, limits the free flow of anticoagulant into the whole blood flow path while preferably not completely stopping the flow of anticoagulant. As set forth in more detail below, the invention may be embodied in the disposable fluid circuit itself or in the combination of the disposable fluid circuit and apheresis device.

The present invention may be embodied, in accordance with one aspect, in a disposable apheresis fluid circuit or system. Such a system may include a separation chamber; a suspension flow path which communicates at one end with the separation chamber and includes a connector at the other end for connecting to a source of cellular suspension, such as blood from a donor/patient or concentrated blood component after initial apheresis processing; an anticoagulant flow path which communicates at one end with the suspension flow path, and includes a connector at the other end for connecting to an anticoagulant source; and a return flow path which communicates at one end with the separation chamber and communicates at the other end with a connector for connection directly to the suspension source or to the suspension flow path for returning one or more suspension components to the source.

In accordance with the present invention, the anticoagulant flow path includes a flow restriction, such as an internal flow restriction, which limits the free flow of anticoagulant into the suspension flow path. For example, it is preferred that the flow restriction limit the free flow of anticoagulant into the suspension flow path to less than about 14–15 milliliters per minute (ml/min) for donor/patient apheresis procedures.

More preferably, the flow restriction limits the free flow of anticoagulant to less than about 12.5 ml/min in a typical donor/patient apheresis procedure, with less than 8 ml/min but more than about 2–3 ml/min being more preferred. In general, an anticoagulant free flow rate of about 5 ml/min is most preferred with converging ranges of between 3–7 ml/min and 4–6 ml/min in order of preference.

In the apheresis field, it is also common to refer to the ratio of the whole blood flow rate to anticoagulant flow rate. This is sometimes referred to as the anticoagulant or AC ratio. In accordance with the present invention it is generally desirable that the flow restriction limit the free flow of anticoagulant to provide an AC ratio of not less than about 7/1 and not more than 13/1 in a free flow situation, i.e., the ratio of the suspension or blood flow rate to anticoagulant free flow rate.

Although the flow restriction may take different forms within the scope of the present invention, in one preferred embodiment an internal flow restriction is provided in the anticoagulant flow path in the form of a tubing segment which is of sufficiently small cross-sectional area and sufficient length to restrict the free flow of anticoagulant therethrough. The anticoagulant flow path may include a tubing segment, for example, which has a lumen from about 0.025 inches to about 0.05 inches in diameter. The required length of the tubing segment will vary inversely with the diameter to provide a given resistance to fluid flow—i.e., a larger diameter tubing will require greater length to provide the same resistance as a smaller diameter tubing.

Although the flow restriction may theoretically be provided at any location in the anticoagulant flow path, it is preferred that the flow restriction in the anticoagulant flow path be downstream of the anticoagulant pump so that pumping ACD at high flow rates does not lead to reduced pressure upstream of the pump of such magnitude that the upstream tubing might collapse and block anticoagulant flow. Also, with the flow restriction between the anticoagulant pump tubing segment and the suspension flow path, the flow restriction retards or restricts the free flow of anticoagulant in free flow conditions while simultaneously allowing the anticoagulant pump to generate enough pressure to pump anticoagulant through the flow restriction at flow rates that are normally used in the regular operation of the apheresis system. The flow restriction should, however, permit such pumped flow of anticoagulant without causing excessive pressure in the anticoagulant flow line. It is generally desired that pumped flow of up to about 14 ml/min of ACD anticoagulant be permitted without creating excessive pressure. Preferably, pumped flow of up to about 14 ml/min should not create pressure substantially greater than about 12 psig in the anticoagulant flow path. Alternatively, it is preferred that flow rates of up to about 12 ml/min be allowed without the pressure exceeding about 7 psig.

Further, although it is desirable to limit the free flow of anticoagulant to prevent excessive anticoagulant from being returned to the donor/patient, it is also desirable to allow at least some small residual flow rate of anticoagulant to prevent clotting. Although such a flow rate may vary with the whole blood flow rate, it is preferred to have a minimum flow rate of between about 3 to 7 ml/min, and preferably about 4–6, with about 5 ml/min being generally most preferred.

Other aspects and details of the present invention are set forth in the attached drawings and the following detailed description of the drawings.

DETAILED DESCRIPTION OF DRAWINGS

Figures 1, 1A:
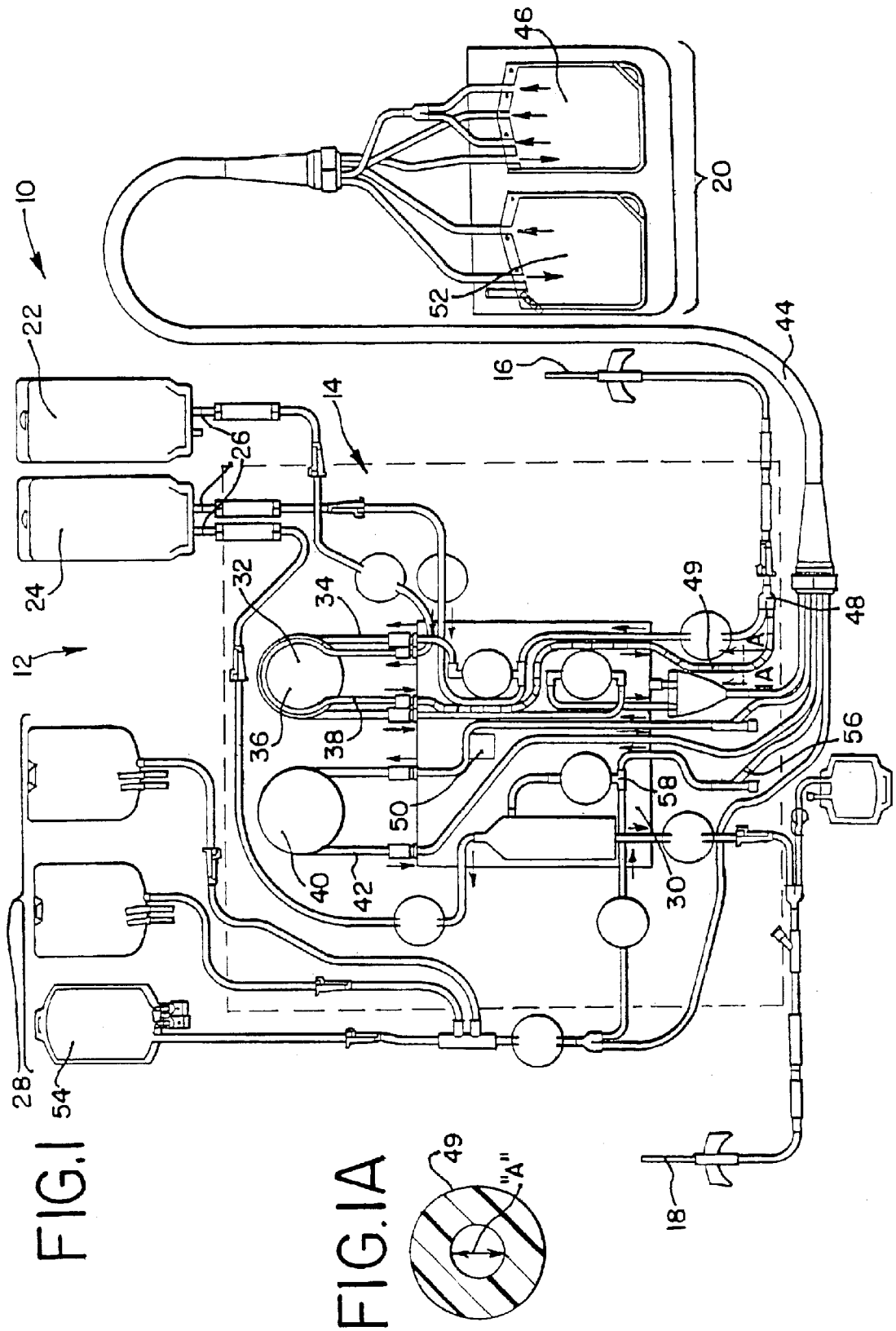
FIG. 1 is a plan view of a dual needle apheresis system embodying the present invention.
FIG. 1A is a cross-sectional view of the anticoagulant flow tubing taken along line 1A—1A in FIG. 1.

FIG. 1 illustrates a dual needle CS-3000 apheresis system 10 embodying the present invention. The apheresis system includes preassembled disposable fluid circuit assembly or system 12 mounted on a reusable CS-3000 centrifuge device 14 illustrated in fragmented and diagrammatic form. A more detailed description of the CS-3000, which has been marketed by Baxter for almost 20 years, may be found in U.S. Pat. Nos. 4,283,004 and 4,526,515 which are incorporated by reference. The CS-3000 will only be set forth in this description to the extent necessary to understand the present invention.

As noted above, the apheresis system shown in FIG. 1 is a dual needle system, which withdraws whole blood from a source, such as a living human donor or patient, through an inlet needle 16 and returns blood components to the donor/patient through a separate return needle 18. The inlet and return needles 16, 18 are typically pre-attached to the tubing set, although the tubing set could terminate in standard needle adapters, such as tapered luer or luer-lock connectors, allowing the user to add their preferred needle.

Although illustrated in a dual needle centrifugal apheresis system in FIG. 1, the present invention is not limited to such a dual needle system or to a centrifugal apheresis system. As discussed in more detail later, the present invention may be used in single needle apheresis systems and in systems which employ different separation chambers and/or principles such as the Cobe Spectra apheresis system, which uses a different style centrifugal separation chamber, or the Baxter Healthcare Autopheresis C, which uses a separation chamber based on a different principle of separation.

The disposable fluid circuit or apheresis system 12 of FIG. 1 includes one or more plastic containers, generally at 20, that are located within the rotating centrifuge chamber of the centrifuge device 14, and form separation chambers in which blood components are separated from one another due to the centrifugal force of the rotating centrifuge chamber.

For priming of the fluid circuit and for anticoagulating whole blood as it is withdrawn from the donor/patient, containers of anticoagulant solution 22 and saline solution 24 are preferably pre-attached to the fluid circuit, which is also sometimes called a tubing set, although they may be provided separately. If pre-attached, the ends of the tubing itself form connectors 26 for connecting or attaching to the containers, as by solvent bonding or the like. If not pre-attached, the tubing may be provided with other types of connectors, such as standard spikes or piercing members, with or without, sub-micron filters, for connecting to the containers. As used herein, "connector" is a generic term that includes, in addition to the above examples of a simple tubing end, spike, and piercing member, any other type or style of connecting means or structure for making fluid connections or attachments.

For collecting one or more blood components from the donor/patient collection containers 28 are preferably pre-attached to the fluid circuit or set. Commonly, more than one container is preattached for collecting different blood components, for example, platelet concentrate and plasma.

To assist in mounting the fluid circuit in a predetermined relationship on the centrifuge device, the disposable apheresis system or fluid circuit includes a housing commonly referred to as a monitor box 30, which contains various sensors and detectors, with tubing extending from and into the top of the housing to form loops for mating with the proper one of the pumps on the centrifuge device 14.

The CS-3000 centrifuge device shown in FIG. 1 has three pumps. The flow of whole blood from the donor/patient into the fluid circuit assembly is controlled by the whole blood pump 32. The whole blood pump is a peristaltic type pump, which operates on a tubing loop or segment 34 of the whole blood flow path to withdraw whole blood from the donor and pump it through the fluid circuit. More specifically, the whole blood pump 32 employs a series of rollers that squeeze the tubing as they roll along the tubing, forcing liquid in the tubing to flow in the direction indicated by the arrows in FIG. 1.

The flow of anticoagulant through the system is controlled by a pump rotor 36 mounted on the same shaft as the whole blood pump rotor 32. The anticoagulant pump is also a peristaltic pump, and operates on a tubing loop or segment 38 of the anticoagulant flow path to pump anticoagulant through the fluid circuit in the direction shown by the arrows in FIG. 1.

The flow of plasma through the system is controlled by plasma pump 40, also a peristaltic pump, which works in conjunction with a tubing loop or segment 42 of the plasma flow path.

In operation, blood is withdrawn by the whole blood pump 32 from a living human donor/patient (not shown) through the inlet needle 16. The whole blood flows from the inlet needle 16 or needle adapter, through the associated plastic tubing, to the whole blood pump 32. Closely downstream of the whole blood inlet needle 16, a junction or coupling 48 is provided in the whole blood tubing for the addition of anticoagulant. The anticoagulant flow path extends from the anticoagulant container 22 to the junction 48 in the whole blood flow path to supply anticoagulant to the whole blood promptly after it is withdrawn from the donor/patient.

From the pump 32, the anticoagulated whole blood is directed through a multilumen umbilicus 44 to a separation container 46 in the centrifuge, which defines a separation chamber in which the whole blood is separated into red cell concentrate and platelet rich plasma. The platelet rich plasma is withdrawn from the separation container and through the umbilicus by the plasma pump 40. After passing through an interface sensor 50, the platelet rich plasma is returned through the umbilicus and into a collection container 52 within the centrifuge bowl or chamber. The collection container forms a separation chamber in which platelet rich plasma is separated into platelet concentrate, which remains in the collection container, and platelet-depleted or component-poor plasma, which is removed from the collection container. A portion of platelet-depleted plasma may be collected in plasma collect bag 54. The remaining plasma is combined with the red cell concentrate, which flows from the separation container 46, through the umbilicus 44 and return line 56 to junction 58, where it is combined with the platelet-depleted plasma and returned to the donor through terminal portion of the return line and return needle 18.

As typically used, the disposable apheresis system 12 shown in FIG. 1 is mounted on the reusable centrifuge device 14, with the anticoagulant and saline solution containers 22 and 24 hooked onto elevated racks above the centrifuge device, as depicted schematically in FIG. 1. The donor or patient is normally reclining in a chair or couch and is below the level of the anticoagulant and saline containers. The difference in height between the anticoagulant solution container and the inlet needle 16 gives rise to a pressure head in the anticoagulant line proportional to the vertical distance between the anticoagulant container and the inlet needle. This liquid head tends to cause anticoagulant to flow from the solution container into the whole blood inlet line. Although this force will be opposed, to some extent, by the venous blood pressure of the donor/patient, it will typically be larger than the venous pressure and tend to cause the flow of anticoagulant into the whole blood line. In addition, blood flow through the blood flow path tends to encourage the flow of anticoagulant into the whole blood flow line.

Although conditions will vary from one donor/patient to another, generally the greatest expected force causing flow of anticoagulant into the whole blood line occurs where there is a full anticoagulant container (and therefore the liquid level highest); the donor/patient's arm is in the lowest normal position, such as about 33 inches from the floor; the donor/patient has very low venous pressure (approaching zero); the donor/patient has a high hematocrit, such as 55; and the whole blood flow rate is high (for example 80–90 ml/min). On the other hand, the minimum expected force would be expected to occur when the anticoagulant container is nearly empty; the donor/patient's arm is in the highest normal position, such as about 36 inches from the floor; the patient/donor has relatively high venous pressure, such as 40 millimeters of mercury; the donor/patient has a low hematocrit such as 20; and the whole blood flow is low (for example 20–35 ml/min). In the event that an operator misinstalls the anticoagulant pump tubing segment 38 in a manner such that an open flow path exists between the anticoagulant container 22 and the junction 48, the forces described above, particularly in the higher force situations, will tend to cause anticoagulant to flow into the whole blood flow path at a much higher rate than is desired.

In accordance with the present invention, the anticoagulant flow line includes a flow restriction which limits the free flow of anticoagulant into the whole blood line in the event that the anticoagulant tubing is improperly or incompletely assembled on the anticoagulant pump in a manner which allows an open flow pathway between the anticoagulant source and the whole blood flow line. The flow restriction may take various forms, such as normally closed check valve that would open only for pressures significantly greater than the pressure from the liquid head of anticoagulant, a mechanical clamp on the flexible tubing that makes up the flow path of the anticoagulant, which would clamp the tubing to restrict the internal passageway, or a section of tubing of reduced lumen diameter to restrict flow.

Although a normally closed check valve may be suitable for preventing the free flow of anticoagulant into the whole blood line, in a free flow situation it may not permit any anticoagulant to flow in the whole blood line. As pointed out earlier, it is desirable to have at least a small minimum flow of anticoagulant into the whole blood line, even in the free flow situation, to prevent coagulation. This nominal free flow rate is preferably between about 3 and 7 ml/min, with 4–6 being more preferable and 5 generally most preferred. A graduated check valve, however, which did not completely cut off anticoagulant flow, but suitably limited the free flow would be a viable alternative to a normally closed check valve.

A mechanical clamp on the anticoagulant flow tubing may also be suitable for restricting the anticoagulant flow path. This would require, however, very close tolerances and mechanical control which would tend to make this an expensive alternative, and any adverse effects of turbulence created by such a clamp would also have to be taken into account.

In accordance with the preferred embodiment of the present invention, an internal flow restriction is provided in the disposable apheresis tubing kit itself. The internal flow restriction may take any form suitable for restricting the free flow of anticoagulant while, preferably, allowing at least a nominal minimum flow. In the illustrated embodiment, however, the entire segment of anticoagulant flow path tubing extending from the return end of the anticoagulant pump segment to the junction 48 is of reduced diameter to create the desired resistance to the flow of anticoagulant. By replacing the entire tubing segment between the return end of the pump segment and the junction 48, the cost to implement the invention is low, and manufacturing simplicity and reliability are achieved.

More specifically, prior to the present invention, the typical polyvinyl chloride plastic tubing in the anticoagulant flow path, for example, from the bag of anticoagulant solution to the monitor box, and from the monitor box to junction 48 had an inside diameter of about 0.095 inches. In accordance with the preferred embodiment of the present invention, the tubing segment 49 between the return end of the pump segment at the monitor box and the junction 48, a length of about 78 inches, has an inside circular lumen or flow path with a diameter of 0.035 inches (0.146 inches OD). This permits a single piece of tubing to be used in place of a prior single piece of tubing, thereby avoiding any extra assembly steps or procedures while providing assured limits on the free flow of anticoagulant.

FIG. 1A is a cross-sectional view of anticoagulant tubing segment 49. As shown in FIG. 1A, the tubing has an interior lumen or bore generally circular in cross-sectional shape, having diameter "A" which is preferably 0.035 inches. The outside diameter of the tube segment is about 0.146 inches, although other outside diameters may be used without departing from this invention.

While plastic PVC tubing having an inside lumen diameter of 0.035 inches and a length of 78 inches is preferred in the illustrated embodiment, other combinations of reduced inside diameters and lengths could be employed to provide sufficient resistance to free flow of anticoagulant and achieve satisfactory results. For example, a tubing segment having an inside diameter of about 0.025 inches and a length of about 20.3 inches would also tend to reduce the free flow of anticoagulant while allowing a certain minimum flow rate under normal conditions. Similarly, a tubing segment having an inside diameter of 0.040 inches and a length of 133 inches also provides sufficient resistance to reduce the anticoagulant free flow rate to approximately 3–7 ml/min.

Generally, the resistance of a tubing segment on anticoagulant free flow may be determined by use of the formula $R=(128 \times L \times U)/(\pi \times d^4)$, where R is the resistance, L is the length, d is the inside diameter of the tubing lumen and U is the viscosity of the anticoagulant. Accordingly, the present invention is not limited to a tubing segment of a particular inside diameter and a particular length, various different diameters and lengths could be used. It is believed that tubing lumen ranging from about 0.025 to 0.05, and 0.03 to 0.045 particularly, depending on the length of tubing segment, would sufficiently restrict the anticoagulant flow rate while allowing at least some nominal flow of anticoagulant into the whole blood flow path in the free flow situation.

It is also preferred in the present invention to employ the flow restriction downstream of the anticoagulant pump, i.e., between the anticoagulant pump segment 38 and the junction 48. When employed in this position, the restriction, while restricting the free flow of anticoagulant, avoids the generation of excessive reduced pressure upstream of the pump in normal operation, while permitting the anticoagulant pump to generate sufficient pressure to pump anticoagulant at the flow rates normally required for routine operation, preferably without causing undue or excessive pressure in the anticoagulant flow path.

Although the amount of pressure that the fluid circuit can safely withstand will depend on the materials and construction of the particular system, generally it is desired that the pressure created by the anticoagulant pump when pumping at the maximum expected flow rate not exceed the pressure employed in the pressure leak testing typically conducted in the manufacturing of these preassembled apheresis systems. In general, and in the CS-3000 system, the maximum expected anticoagulant flow pump rate is not more than about 12–14 ml/min, which assumes a whole blood flow rate of 88 ml/min and an AC ratio or not less than about 6/1–7/1. At such an anticoagulant pump rate, it is preferred that the pressure in the anticoagulant flow path not substantially exceed about 12 psig. More preferably, the flow restriction should not create pressure greater than about 7 psig when the anticoagulant flow rate is 12 ml/min.

FIG. 1 depicts an apheresis systems in which blood is withdrawn from a donor/patient through one needle and returned to the donor/patient through another needle. Baxter Healthcare Corporation, Cobe Laboratories, and others also provide an alternative disposable apheresis system, commonly referred to as a single needle system, which operates on an intermittent cycle, withdrawing blood from the donor/patient, processing the blood to separate the desired blood components and then returning the undesired blood components to the donor/patient through the same needle that it is withdrawn. The single needle CS-3000 apheresis system is constructed much like the system described above in FIG. 1. However, in the single needle system the blood component return line is connected directly with the whole blood flow line instead of into a separate needle. Typically the return line is connected by a junction, manifold or other connection, to the whole blood between the needle and the anticoagulant junction, for returning blood components to the donor during the return cycle in the single needle procedure.

Figure 2:
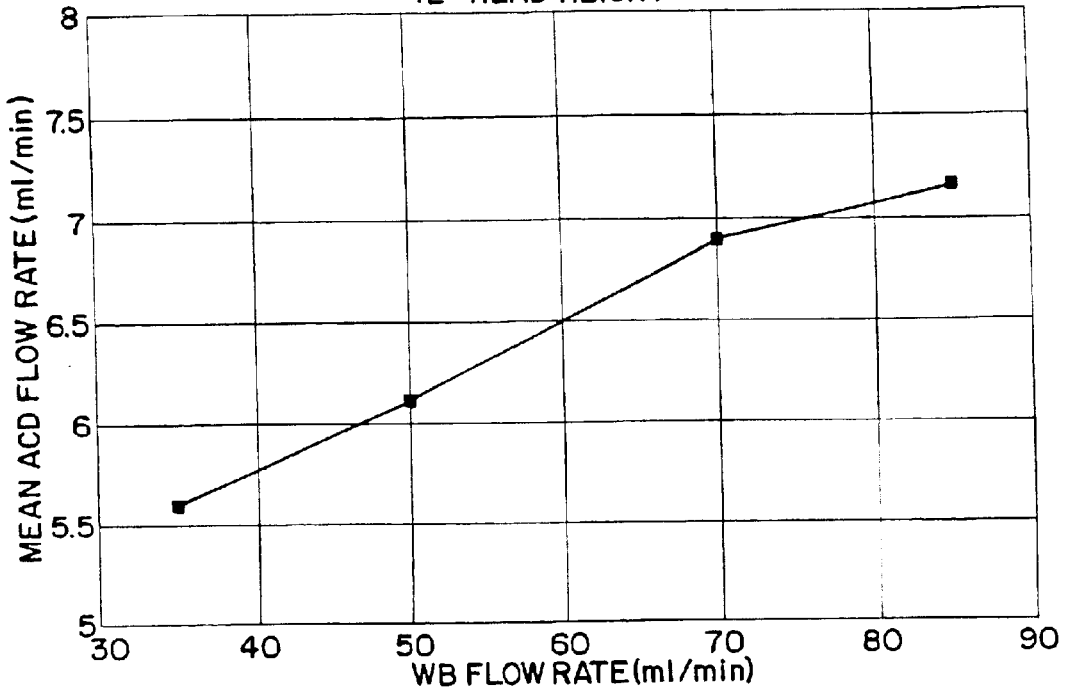
FIG. 2 is a graph of the simulated anticoagulant free flow rate versus whole blood flow rate in an apheresis system embodying the present invention when the simulated anticoagulant source is located 42 inches above the suspension or whole blood inlet.

Turning now to FIG. 2, the graph shown there illustrates simulated anticoagulant free flow rate relative to the whole blood flow rate in apheresis system using the preferred embodiment of the present invention (with a tubing segment of 0.035 inches inside diameter and a length of 78 inches) in what may be generally regarded as a high free flow situation, with a 42 inch liquid pressure head and employing bovine blood. As can be seen from that chart, as a result of the present invention, the free anticoagulant flow rate does not exceed 7.5 ml/min even at a whole blood flow rate of 80 ml/min, and not less than about 5.5 ml/min at the lowest whole blood flow rates. Accordingly, in the event the anticoagulant pump segment 38 in the system of FIG. 1 is improperly installed on the anticoagulant pump 36, and a free flow condition created, the free anticoagulant flow rate would be well within acceptable limits even at the highest whole blood flow rates,—and even with a very large liquid head tending to force anticoagulant fluid into the whole blood flow path.

Figure 3:
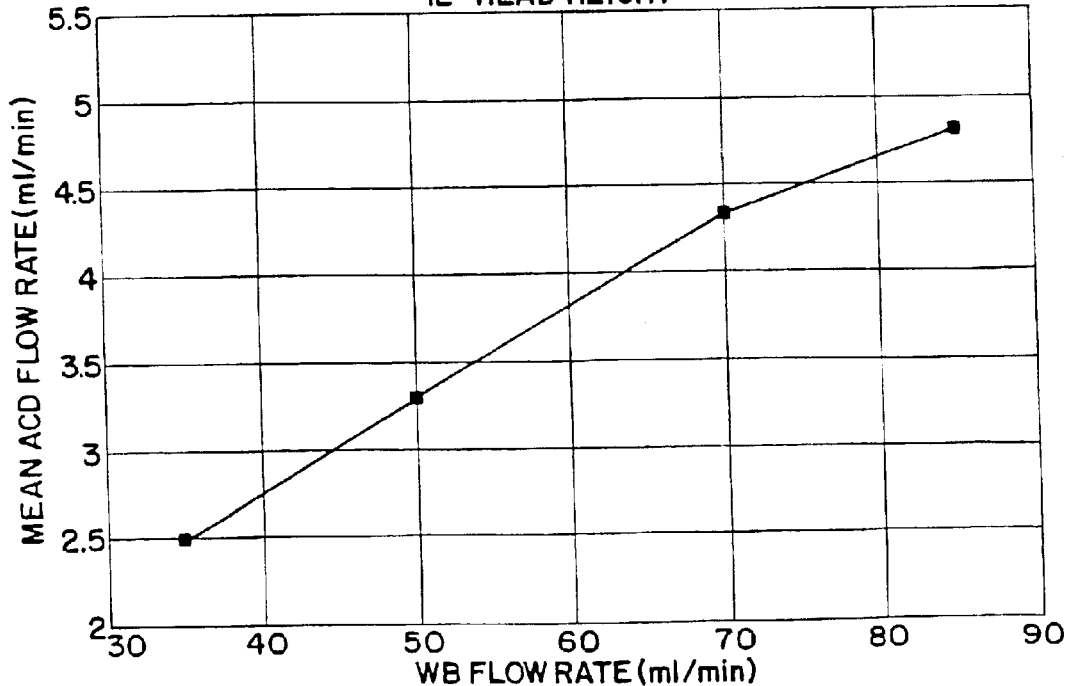
FIG. 3 is a graph of the simulated anticoagulant free flow rate versus whole blood flow rate in an apheresis system embodying the present invention when the simulated anticoagulant source is located 12 inches above the suspension or whole blood inlet.

FIG. 3 is a similar graph, depicting simulated free anticoagulant flow rate versus whole blood flow rate in a apheresis system employing the preferred embodiment of the present invention as illustrated in FIG. 1, where the liquid head tending to force anticoagulant solution into the whole blood flow path is 12 inches and also bovine blood. It may be seen there that the anticoagulant flow rate is not less than about 2.5 at the low whole blood flow rate and not greater than about 5 ml/min at the highest simulated whole blood flow rate of 80 ml/min.

While the present invention has been described in connection with the disposable apheresis system employed in the CS-3000 centrifuge manufactured and sold by Baxter Healthcare Corporation, the present invention may also be employed in other apheresis systems, centrifugal and non-centrifugal, which are subject to possible excessive anticoagulant flow rates in the event of operator misassembly without departing from the present invention.

For example, in the Cobe Spectra apheresis system, a flow restriction in accordance with the present invention could be provided in the anticoagulant tubing between the anticoagulant pump and the manifold where it joins the whole blood inlet flow line. Although not actually tested, it is anticipated that tubing diameters and lengths as described above, would also be generally suitable for use in the Spectra disposable system to provide the desired limitation on the free flow of anticoagulant in the event of misassembly or mechanical failure while also allowing a nominal flow of anticoagulant into the whole blood path and without creating undue pressure when the device is in normal use. It is therefore clear that although the present invention has been described in terms of the preferred and alternative embodiments, the present invention has application in many other apheresis systems and applications, as will be appreciated by persons skilled in the apheresis field. For these reasons, the scope of the present invention is not limited to the specific embodiments illustrated, but is as defined in the appended claims.

What is claimed is:

1. A disposable centrifugal apheresis system for use in a centrifuge, said system comprising
   a separation chamber;
   a whole blood flow path communicating at one end with said chamber and including a connector at the other end for connecting to a blood vessel in a living human, said whole blood tubing including flexible plastic tubing comprising a pump segment for cooperating with a peristaltic pump on the centrifuge for pumping whole blood through said whole blood flow path;
   an anticoagulant flow path communicating at one end with said whole blood flow path and including another end for connecting to an anticoagulant source, said one end of the anticoagulant flow path communicating with said whole blood flow path at a single location relatively close to said other end of the whole blood flow path, said anticoagulant flow path including flexible plastic tubing comprising a pump segment for cooperating with a peristaltic pump for pumping anticoagulant through said anticoagulant flow path;
   a return flow path communicating at one end with said chamber and communicating at the other end with selected one of a connector for connection to the human and said whole blood flow path for returning one or more components to the human; and
   said anticoagulant flow path between said pump segment and said whole blood flow path including a fixed and non-variable flow restriction to limit the free flow of anticoagulant into said whole blood flow path and thereby limit but not completely block the amount of anticoagulant that may be returned to the human source.

2. A disposable apheresis system in accordance with claim 1 in which said flow restriction limits the free flow of anticoagulant to less than about 13 milliliters per minute.

3. A disposable apheresis system in accordance with claim 1 in which said flow restriction limits the free flow of anticoagulant to between about 3 and 7 milliliters per minute.

4. A disposable apheresis system in accordance with claim 1 in which said flow restriction limits the free flow of anticoagulant to between about 5 and 6 milliliters per minute.

5. A disposable apheresis system in accordance with claim 1 in which said flow restriction limits the free flow of anticoagulant to provide a ratio of blood pumped flow rate to anticoagulant free flow rate of not less than about 7/1.

6. A disposable centrifugal blood separation system in accordance with claim 1 in which said flow restriction limits the free flow of anticoagulant to provide a ratio of blood pumped flow rate to anticoagulant free flow rate of between about 7/1 and 13/1.

7. A disposable centrifugal blood separation system in accordance with claim 1 in which said flow restriction limits the free flow of anticoagulant to provide a ratio of suspension flow rate to anticoagulant free flow rate of not greater than about 13/1.

8. A disposable apheresis system in accordance with claim 1 in which said flow restriction allows pumped flow of anticoagulant at a flow rate of up to about 14 milliliters per minute without creating undue pressure in said anticoagulant flow path.

9. A disposable apheresis system in accordance with claim 1 in which said flow restriction allows pumped flow of anticoagulant at a flow rate of up to about 14 milliliters per minute without creating pressure in said anticoagulant flow path substantially in excess of about 12 psig.

10. A disposable apheresis system in accordance with claim 1 in which said flow restriction allows pumped flow of anticoagulant at a flow rate of up to about 12 milliliters per minute without creating pressure in said anticoagulant flow path in excess of about 7 psig.

11. A disposable apheresis system in accordance with claim 1 in which said flow restriction comprises a tubing segment having a lumen of between about 0.025 and 0.05 inches in diameter.

* * * * *